United States Patent
Nagai et al.

(12) 
(10) Patent No.: US 7,223,587 B2
(45) Date of Patent: May 29, 2007

(54) GENE CONFERRING LYSOZYME INSENSITIVITY TO CORYNEBACTERIUM

(75) Inventors: Kazuo Nagai, Tokyo (JP); Masaaki Wachi, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/942,018

(22) Filed: Sep. 16, 2004

(65) Prior Publication Data

US 2005/0054062 A1 Mar. 10, 2005

Related U.S. Application Data

(62) Division of application No. 09/786,474, filed as application No. PCT/JP98/03981 on Sep. 4, 1998, now Pat. No. 6,855,516.

(51) Int. Cl.
 *C12N 1/20* (2006.01)
 *C12N 15/74* (2006.01)
(52) U.S. Cl. .................. 435/252.32; 435/471
(58) Field of Classification Search .............. 435/4; 530/350
 See application file for complete search history.

(56) References Cited

U.S. PATENT DOCUMENTS 4,617,267 A 10/1986 Katsumata et al.
4,681,847 A 7/1987 Katsumata et al.

FOREIGN PATENT DOCUMENTS

| JP | 54-122794 |   | 9/1979 |
|---|---|---|---|
| JP | 58-56678 A |   | 4/1983 |
| JP | 62-44171 | * | 2/1987 |
| JP | 62-49038 |   | 10/1987 |
| JP | 62-49038 B |   | 10/1987 |
| JP | 1-29555 |   | 6/1989 |
| JP | 1-29555 B |   | 6/1989 |

OTHER PUBLICATIONS

Takashi Hirasawa et al.: "Analysis of Lysozyme-Sensitive Mutants of Coryneform Bacteria," Nippon Nōgeikagaku Kaishi, Mar. 1998, vol. 72 (Abstracts), p. 47.
Takashi Hirasawa et al.: "Analysis of Lysozyme-Sensitive Mutants of Coryneform Bacteria," Nippon Nōgeikagaku Kaishi, Mar. 1998, vol. 72 (Abstracts), p. 47.

* cited by examiner

Primary Examiner—Karen Cochrane Carlson
Assistant Examiner—Suzanne M. Noakes
(74) Attorney, Agent, or Firm—Foley & Lardner LLP

(57) ABSTRACT

The present invention relates to a protein having an activity of giving a lysozyme insensitivity to a lysozyme-sensitive microorganism belonging to *Corynebacterium glutamicum*; DNA which codes for the protein; a recombinant vector containing the DNA; a transformant obtained by introducing the recombinant vector into a host cell; a bacterium having a lysozyme sensitivity in which the activity of the protein is inactivated; and a method for producing an amino acid using the bacterium.

4 Claims, 2 Drawing Sheets

GENE CONFERRING LYSOZYME INSENSITIVITY TO *CORYNEBACTERIUM*

CROSS REFERENCE TO RELATED APPLICATIONS

This application is a division of application Ser. No. 09/786,474 filed Mar. 5, 2001, now U.S. Pat No. 6,855,516 which is a US National Phase Application of PCT application No. PCT/JP98/03981 filed Sep. 4, 1998.

TECHNICAL FIELD

The present invention relates to a gene which codes for a protein having an activity of giving a lysozyme insensitivity to a lysozyme-sensitive microorganism belonging to *Corynebacterium glutamicum*. The bacterium having lysozyme-sensitivity which is obtained by inactivating the gene is useful for the production of amino acids, etc.

BACKGROUND ART

Lysozyme-sensitive variants belonging to genus *Corynebacterium* are used for the manufacture of glutamic acid (Examined Published Japanese Patent Application (JP-B) No. Hei 1-29555) and of glutamine (JP-B Sho 62-49038) and are also used as hosts for the preparation of transformants (Unexamined Published Japanese Patent Application (JP-A) No. Sho 58-56678).

Microorganisms belonging to the genus *Corynebacterium* and having a sensitivity to lysozyme have been prepared by random introduction of mutation into a chromosome with a mutagenizing agent, followed by a selection of lysozyme-sensitive mutant(s) from the resulting strains (JP-B Sho 62-49038 and Hei 1-29555 and JP-A Sho 58-56678). According to such a method, however, in addition to the mutation concerning the lysozyme sensitivity, unfavorable mutation can also be accompanied therewith and, therefore, it is difficult to obtain a desired lysozyme-sensitive microorganism efficiently.

DISCLOSURE OF THE INVENTION

The present invention relates to the following (1) to (19).

(1) A DNA coding for a protein which comprises the amino acid sequence of SEQ ID NO: 2, or a protein which copmprises the amino acid sequence of SEQ ID NO: 2 where one or more amino acids are deleted, substituted, or added and which has an activity of giving a lysozyme insensitivity to a lysozyme-sensitive microorganism belonging to *Corynebacterium glutamicum*.

(2) A DNA coding for a protein which comprises an amino acid sequence having 60% or more homology to the amino acid sequence of SEQ ID NO: 2 and which has an activity of giving a lysozyme insensitivity to a lysozyme-sensitive microorganism belonging to *Corynebacterium glutamicum*.

(3) A DNA comprising the nucleotide sequence of SEQ ID NO: 1, or a DNA hybridizing with the DNA of SEQ ID NO: 1 under stringent conditions and coding for a protein which has an activity of giving a lysozyme insensitivity to a lysozyme-sensitive microorganism belonging to *Corynebacterium glutamicum*.

(4) A DNA which is contained in a plasmid carried by FERM BP-6479 and codes for a protein which has an activity of giving a lysozyme insensitivity to a lysozyme-sensitive microorganism belonging to *Corynebacterium glutamicum*.

(5) The DNA according to any one of (1) to (4), wherein the protein which has an activity of giving a lysozyme insensitivity to a lysozyme-sensitive microorganism belonging to *Corynebacterium glutamicum* is a protein having an activity of giving an insensitivity to 100 µg/ml lysozyme to a mutant belonging to *Corynebacterium glutamicum* and having a sensitivity to not more than 50 µg/ml lysozyme.

(6) The DNA according to any one of (1) to (5), wherein the DNA is a DNA derived from a microorganism belonging to the genus *Corynebacterium*.

(7) The DNA according to any one of (1) to (5), wherein the DNA is a DNA derived from a microorganism belonging to *Corynebacterium glutamicum*.

(8) A recombinant vector comprising the DNA according to any one of (1) to (7).

(9) A transformant prepared by introducing the recombinant vector of (8) into a host cell.

(10) A protein which comprises the amino acid sequence of SEQ ID NO: 2, or a protein which comprises the amino acid sequence of SEQ ID NO: 2 where one or more amino acids are deleted, substituted, or added and which has an activity of giving a lysozyme insensitivity to a lysozyme-sensitive microorganism belonging to *Corynebacterium glutamicum*.

(11) A protein which comprises an amino acid sequence having 60% or more homology to the amino acid sequence of SEQ ID NO: 2 and which has an activity of giving a lysozyme insensitivity to a lysozyme-sensitive microorganism belonging to *Corynebacterium glutamicum*.

(12) The protein according to (10) or (11), wherein the protein which has an activity of giving a lysozyme insensitivity to a lysozyme-sensitive microorganism belonging to *Corynebacterium glutamicum* is a protein having an activity of giving an insensitivity to 100 µg/ml lysozyme to a mutant belonging to *Corynebacterium glutamicum* and having a sensitivity to not more than 50 µg/ml lysozyme.

(13) A method for producing the protein of any one of (10) to (12), which comprises culturing the transformant of (9) in a medium, producing and accumulating the protein in the culture, and collecting the protein from the culture.

(14) A method for the preparation of a bacterium having a lysozyme sensitivity, which comprises inactivating the activity of the protein of any one of (10) to (12).

(15) The method according to (14), wherein a mutation is introduced into a chromosomal gene coding for the protein of any one of (10) to (12).

(16) The method according to (14) or (15), wherein the bacterium is a microorganism belonging to the genus *Corynebacterium*.

(17) A bacterium obtainable by the method of any one of (14) to (16).

(18) A method for producing an amino acid, which comprises culturing the bacterium of (17) in a medium, producing and accumulating an amino acid in the culture, and collecting the amino acid from the culture.

(19) The method according to (18), wherein the amino acid is glutamic acid or glutamine.

The DNA of the present invention is a DNA coding for a protein which has an activity of giving a lysozyme insensitivity to a lysozyme-sensitive microorganism belonging to *Corynebacterium glutamicum*, and its examples are the DNAs coding for the proteins of the present invention as mentioned below or, to be more specific, the DNA having the nucleotide sequence shown by SEQ ID NO: 1.

Another example of the DNA of the present invention is a DNA hybridizing with the DNA coding for the protein of the present invention under stringent conditions.

The "DNA hybridizing under stringent conditions" used herein means, for example, a DNA which is obtained by means of a colony hybridization, a plaque hybridization, a southern blot hybridization, and so on using the DNA having the nucleotide sequence shown by SEQ ID NO: 1 as a probe. A specific example is a DNA which is able to be identified by hybridizing at 65° C. in the presence of 0.7 to 1.0 M sodium chloride by the use of a filter where DNA derived from colony or plaque is immobilized followed by washing the filter under the condition of 65° C. by the use of 0.1- to 2-fold concentration of an SSC solution (where an SSC solution of a 1-fold concentration is composed of 150 mM sodium chloride and 15 mM sodium citrate).

A hybridization can be carried out according to the methods described, for example, in "Molecular Cloning, A Laboratory Manual" Second Edition, Cold Spring Harbor Laboratory Press (1989) (hereinafter, referred to as "Molecular Cloning Second Edition"), "Current Protocols in Molecular Biology" John Wiley & Sons (1987–1997) (hereinafter, referred to as "Current Protocols in Molecular Biology"), "DNA Cloning 1: Core Techniques. A Practical Approach" Second Edition, Oxford University Press (1995), etc.

Specifically, the hybridizable DNA is a DNA having at least 60% or more homology, preferably, 80% or more homology, or, more preferably, 95% or more homology to the nucleotide sequence shown by SEQ ID NO: 1.

Examples of the protein of the present invention are a protein comprising the amino acid sequence shown by SEQ ID NO: 2; a protein which comrpises the amino acid sequence shown by SEQ ID NO: 2 where one or more amino acids are deleted, substituted, or added and which has an activity of giving a lysozyme insensitivity to a lysozyme-sensitive microorganism belonging to Corynebacterium glutamicum; and a protein which comprisess an amino acid sequence having 60% or more homology to the amino acid sequence shown by SEQ ID NO: 2 and which has an activity of giving a lysozyme insensitivity to a lysozyme-sensitive microorganism belonging to Corynebacterium glutamicum.

A protein which comprises the amino acid sequence shown by SEQ ID NO: 2 where one or more amino acids are deleted, substituted, or added and which has an activity of giving a lysozyme insensitivity to a lysozyme-sensitive microorganism belonging to Corynebacterium glutamicum may be prepared by site-directed mutagenesis of a DNA coding for a protein having an amino acid sequence shown, for example, by SEQ ID NO: 2 using a method for site-directed mutagenesis described, for example, in Molecular Cloning Second Edition; Current Protocols in Molecular Biology; Proc. Natl. Acad. Sci., USA, 79, 6409 (1982); Gene, 34, 315 (1985); Nucleic Acids Research, 13, 4431 (1985); Proc. Natl. Acad. Sci., USA, 82, 488 (1985); etc.

There is no particular limitation on the numbers of amino acid(s) which is/are deleted, substituted, or added, although one to several tens amino acid(s) is/are preferred. One to several amino acid(s) is/are more preferred. It is preferred that the resulting amino acid sequence has at least 60% or more, usually not less than 80%, or, particularly, not less than 95% of homology to the amino acid sequence of SEQ ID NO: 2.

The present invention will now be further illustrated below.

(1) Preparation of Chromosomal DNA and Recombinant Vector

The DNA of the present invention may be prepared from a lysozyme-insensitive strain belonging to the genus Corynebacterium.

With regard to a lysozyme-insensitive strain belonging to the genus Corynebacterium, any strain such as Corynebacterium glutamicum ATCC 13032 strain, KY 9611 strain, and such may be used so far as the strain well grows even when 100 μg/ml lysozyme is present in a medium.

The lysozyme-insensitive strain belonging to the genus Corynebacterium can be cultured by a known method described, for example, in Appl. Microbiol. Biotechnol., 39, 318 (1993).

After culturing, the chromosomal DNA of the microorganism is isolated and purified according to a known method such as that mentioned in "Current Protocols in Molecular Biology," John Wiley & Sons (1987–1997) or Agric. Biol. Chem. 49, 2925 (1985).

The resulting chromosomal DNA is cleaved using an appropriate restriction enzyme, and the resulting DNA fragments are inserted into a vector for Corynebacterium by a conventional method as described in Molecular Cloning Second Edition, to prepare a recombinant vector.

With regard to the vector, any vector may be used as long as it is able to autonomously replicate in a microorganism belonging to the genus Corynebacterium, and its examples are pCG1 (JP-A Sho 57-134500), pCG2 (JP-A Sho 58-35197), pCG4 and pCG11 (both in JP-A Sho 57-183799), pCE53 and pCB101 (both in JP-A Sho 58-105999), pCE51, pCE52, and pCE53 [all in Mol. Gen. Genet., 196, 175 (1984)], pAJ1844 (JP-A Sho 58-21619), pHK4 (JP-A Hei 7-20399), pHM1519 [Agric. Biol. Chem., 48, 2901 (1985)], pCV35 and pECM1 [both in J. Bacteriol., 172, 1663 (1990)], and pC2 [Plasmid, 36, 62 (1996)].

(2) Preparation of the DNA of the Present Invention

The recombinant vector prepared as described above is introduced into a lysozyme-sensitive microorganism belonging to Corynebacterium glutamicum.

With regard to a lysozyme-sensitive microorganism belonging to Corynebacterium glutamicum, any of wild strain and mutant strain may be used as long as it belongs to Corynebacterium glutamicum and exhibits a lysozyme sensitivity. Among the microorganisms belonging to Corynebacterium glutamicum, a wild strain is not usually affected at all for its growth even when 100 μg/ml lysozyme is present in a medium or, in other words, the strain is mostly insensitive to lysozyme. Therefore, a mutant is usually used as a lysozyme-sensitive microorganism.

When lysozyme in a concentration of as low as not more than 50 μg/ml is present in a medium, growth of a lysozyme-sensitive microorganism is usually inhibited.

Lysozyme-sensitive microorganisms can be isolated from Corynebacterium glutamicum as a parent strain according to a known method (JP-B Sho 62-49038 and Hei 1-29555 and JP-A Sho 58-56678). Examples of such a mutant are Corynebacterium glutamicum ATCC 31834 strain (FERM P-5946) (JP-A Sho58-56678), KY9714 strain, KY11939 strain, KY11940 strain, and KY11941 strain derived from Corynebacterium glutamicum KY9611 strain; and KY9704 strain and KY9706 strain derived from Corynebacterium glutamicum ATCC 13032 strain.

As to a method for introduction of the recombinant vector, any method may be used as long as it can introduce DNA into the above-mentioned host cells, and its examples are protoplast method [JP-A Sho 57-186492 and Sho 58-56678; J. Bacteriol., 159, 306 (1984)] and electroporation method (JP-A Hei 2-207791). Alternatively, a chromosomal DNA library of lysozyme-insensitive strain belonging to the genus Corynebacterium can be prepared using Escherichia coli, followed by introducing the recombinant vector into a lysozyme-sensitive microorganism of *Corynebacterium glutamicum* by means of a conjugal transfer of the *E. coli* according to a known method [*J. Bacteriol.*, 172, 1663 (1990); *J. Bacteriol.*, 178, 5768 (1996)].

A lysozyme-sensitive microorganism of *Corynebacterium glutamicum* into which a recombinant vector has been introduced is cultured usually at 20 to 39° C. for 24 to 72 hours in a medium containing 100 µg/ml lysozyme such as LB medium [10 g/l Bactotrypton (manufactured by Difco), 5 g/l yeast extract (manufactured by Difco), and 5 g/l sodium chloride; pH 7.2] containing 100 µg/ml lysozyme. After culturing, the strain grown in the medium is selected as a strain having the desired DNA.

Growth of the lysozyme-sensitive microorganism is sometimes temperature-sensitive. The lysozyme-sensitive microorganism whose growth is temperature-sensitive is not able to grow at a high temperature (such as 34 to 39° C.) even when lysozyme is absent in the medium. In that case, a strain which grows at the temperature where the lysozyme-sensitive microorganism is unable to grow such as at 34 to 39° C. or, preferably, at 36 to 38° C. in a medium containing no lysozyme can be selected as a strain having the desired DNA.

Examples of such a mutant are *Corynebacterium glutamicum* KY9714 strain and KY11941 strain which are derived from *Corynebacterium glutamicum* KY9611 strain; KY9704 strain and KY9706 strain which are derived from *Corynebacterium glutamicum* ATCC 13032 strain.

The resulting DNA may be incorporated into a vector by a conventional method either as it is or after being cleaved by an appropriate restriction enzyme or the like and then analyzed for its nucleotide sequence by a commonly used method such as dideoxy method [*Proc. Natl. Acad. Sci. USA*, 74, 5463 (1977)] or by using a nucleotide sequence analyzing apparatus such as a 373A DNA Sequencer (manufactured by Perkin-Elmer), to determine the nucleotide sequence of the DNA.

Examples of the vector into which the DNA is incorporated are pBluescript KS(+) (manufactured by Stratagene), pDIRECT [*NucleicAcids Research*, 18, 6069 (1990)], pCR-Script Amp SK(+) (manufactured by Stratagene), pT7Blue (manufactured by Novagen), pCRII (manufactured by Invitrogen), pCR-TRAP (manufactured by Gene Hunter), and pNoTAT7 (manufactured by 5 Prime→3 Prime).

Examples of a DNA having a novel nucleotide sequence obtained as mentioned above are DNAs having the sequences shown by SEQ ID NO: 1 and SEQ ID NO: 3.

A DNA having the nucleotide sequence of SEQ ID NO: 1 encodes a protein having the amino sequence of SEQ ID NO: 2.

Examples of a strain harboring a plasmid comprising the DNA having the sequence of SEQ ID NO: 1 are *Corynebacterium glutamicum* KY9714/pHLS2 and *Corynebacterium glutamicum* KY9714/pHLS4.

It is also possible that a primer based on the nucleotide sequence determined as described above is prepared and then a desired DNA is obtained by means of PCR [PCR Protocols, Academic Press (1990)] using a chromosomal DNA as a template.

A desired DNA can also be prepared by chemical synthesis, based on the determined nucleotide sequence of the DNA, using a DNA Synthesizer (Type 8905 manufactured by Perceptive Biosystems) or the like.

(3) Production of the Protein of the Present Invention

The protein of the present invention may be produced by expression of the DNA of the present invention in host cells using the method described in Molecular Cloning Second Edition, Current Protocols in Molecular Biology, and such, for example, by the following manner.

Based on a full-length cDNA, if necessary, a DNA fragment of an appropriate length containing a region coding for the protein is prepared.

The DNA fragment or the full-length cDNA is inserted downstream of a promoter of an appropriate expression vector to prepare a recombinant vector.

By introducing the recombinant vector into host cells suitable for the expression vector, a transformant which produces the protein of the present invention can be obtained.

With regard to a host cell, any cell may be used as long as it is capable of expressing the desired gene. Such a host cell includes bacteria, yeast, animal cells, insect cells, plant cells, etc.

An expression vector that can be used is autonomously replicable in the above host cell or is able to be integrated into chromosomes and contains a promoter at the position where the DNA coding for the protein of the present invention is transcribed.

When a prokaryote such as bacteria is used as a host cell, it is preferred that the recombinant vector containing the DNA coding for the protein of the present invention is autonomously replicable in the host and that, and contains a promoter, a ribosome-binding sequence, the DNA coding for the protein of the present invention, and a transcription termination sequence. The vector may also contain a gene that regulates the promoter.

Examples of the expression vector are pBTrp2, pBTac1, and pBTac2 (all sold by Boehringer-Mannheim); pKK233-2 (Pharmacia); pSE280 (Invitrogen); pGEMEX-1 (Promega); pQE-8 (Qiagen); pKYP10 (JP-A Sho 58-110600); pKYP200 [*Agric. Biol. Chem.*, 48, 669(1984)]; pLSA1 [*Agric. Biol. Chem.*, 53, 277 (1989)]; pGEL1 [*Proc. Natl. Acad. Sci. USA*, 82, 4306 (1985)]; pBluescript II SK(−) (Stratagene); pTrs30 [prepared from *Escherichia coli* JM109/pTrS30 (FERM BP-5407)]; pTrs32 [prepared from *Escherichia coli* JM109/pTrS32 (FERM BP-5408)]; pGHA2 [prepared from *Escherichia coli* IGHA2 (FERM BP-400), JP-A Sho 60-221091]; pGKA2 [prepared from *Escherichia coli* IGKA2 (FERM BP-6798), JP-A Sho 60-221091]; pTerm2 (U.S. Pat. Nos. 4,686,191, 4,939,094, and 5,160,735); psupex, pUB110, pTP5, pC194, and pEG400 [*J. Bacteriol.*, 172, 2392(1990)]; pGEX (Pharmacia); pET system (Novagen); and pSupex.

With regard to a promoter, any promoter may be used as long as it is able to function in host cells, and its examples are promoters derived from *Escherichia coli*, phage, and so on, such as trp promoter ($P_{trp}$), lac promoter, $P_L$ promoter, $P_R$ promoter, and T7 promoter. It is also possible to use artificially designed and modified promoters such as a promoter where two $P_{trp}$ are connected in tandem ($P_{trp}$×2) tac promoter, lacT7 promoter, and letI promoter.

It is preferred to use a plasmid where the distance between an initiation codon and Shine-Dalgarno sequence, which is a ribosome-binding sequence, is adjusted appropriately (for example, 6 to 18 bases).

It is possible to improve the productivity of the protein of the present invention by substituting base(s) in the nucleotide sequence in the region coding for the protein so as to give a codon which is optimum for expression of the protein in the host.

In the recombinant vector of the present invention, although a transcription termination sequence is not always necessary for expression of the DNA of the present invention, it is preferred to place a transcription termination sequence immediately downstream of the structural gene.

Examples of the host cell are microorganisms belonging to the genus *Escherichia*, the genus *Serratia*, the genus *Bacillus*, the genus *Brevibacterium*, the genus *Corynebacterium*, the genus *Microbacterium*, and the genus *Pseudomonas*, such as *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Serratia ficaria*, *Serratia fonticola*, *Serratia liquefaciens*, *Serratia marcescens*, *Bacillus subtilis*, *Bacillus amyloliquefaciens*, *Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium acetoacidophilum* ATCC 13870, *Microbacterium ammoniaphilum* ATCC 15354, *Pseudomonas* sp. D-0110, and the like.

A recombinant vector can be introduced into the above-mentioned host cells by any of methods for the introduction of DNA, for example, a method using calcium ion [*Proc. Natl. Acad. Sci. USA,* 69, 2110 (1972)], protoplast method (JP-A Sho 63-2483942), and the methods described in *Gene,* 17, 107 (1982) and *Molecular & General Genetics,* 168, 111 (1979).

When yeast is used as a host cell, examples for expression vector are YEP13 (ATCC 37115), YEp24 (ATCC 37051), and YCp 50 (ATCC 37419).

With regard to a promoter, any promoter may be used as long as it is able to function in yeast strains, and its examples are promoters of genes of a glycolytic pathway such as hexokinase, PH05 promoter, PGK promoter, GAP promoter, ADH promoter, gal 1 promoter, gal 10 promoter, heat shock protein promoter, MFα1 promoter, and CUP 1 promoter.

Examples of the host cell are microorganisms belonging to the genus *Saccharomyces*, the genus *Kluyveromyces*, the genus *Trichosporon*, and the genus *Schwanniomyces*, such as *Saccharomyces cerevisiae*, *Schizosaccharomyces pombe*, *Kluyveromyces lactis*, *Trichosporon pullulans*, and *Schwanniomyces alluvius*.

A recombinant vector can be introduced into yeast by any method as long as it enables introduction of DNA into yeast. Such a method includes electroporation method [*Methods. Enzymol.,* 194, 182 (1990)], spheroplast method [*Proc. Natl. Acad. Sci. USA,* 84,. 1929 (1978)], lithium acetate method [*J. Bacteriology,* 153, 163 (1983)], and the method described in *Proc. Natl. Acad. Sci. USA,* 75, 1929 (1978).

When an animal cell is used as a host, examples of an expression vector are pcDNAI, pcDM8 (commercially available from Funakoshi), pAGE107 [JP-A Hei 3-22979; *Cytotechnology,*.3, 133 (1990)], pAS3-3 (JP-A Hei 2-227075), pCDM8 [*Nature,* 329, 840 (1987)], pcDNAI/Amp (Invitrogen), pREP4 (Invitrogen), pAGE103 [*J. Biochemistry,* 101, 1307 (1987)], and pAGE210.

With regard to a promoter, any promoter may be used as long as it is able to function in animal cells, such as the promoter of immediate early (IE) gene of cytomegalovirus (CMV), early promoter of SV40, promoter of retrovirus, metallothionein promoter, heat shock promoter, and SRα promoter. It is also possible to use an enhancer for IE gene of human CMV together with a promoter.

Examples of the host cell are Namalwa cell, which is a human cell, COS cell, which is a simian cell, CHO cell, which is a cell of Chinese hamster, and HBT 5637 (JP-A Sho 63-299).

A recombinant vector can be introduced into animal cells by any method as long as the method enables introduction of DNA into animal cells, and its examples are electroporation method [*Cytotechnology,* 3, 133 (1990)], calcium phosphate method (JP-A Hei 2-227075), and lipofection method [*Proc. Natl. Acad. Sci. USA,* 84, 7413 (1987)].

When an insect cell is used as a host, it is possible to express a protein by the method described, for example, in "Current Protocols in Molecular Biology," "Baculovirus Expression Vectors, A Laboratory Manual," W. H. Freeman and Company, New York (1992), and *Bio/Technology,* 6, 47 (1988).

Thus, a recombinant gene-introducing vector and a baculovirus are co-transfected into an insect cell to give a recombinant virus in a supernatant of insect cell culture, and then a recombinant virus is further infected to another insect cell to express a protein.

Examples of the gene-introducing vector used in such a method are pVL 1392, pVL 1393, and pBlueBacIII (all from Invitrogen).

Baculoviruses that can be used include, for example, *Autographa californica* nuclear polyhedrosis virus, which is a virus infecting to insects belonging to the subfamily Hadeninae.

Examples of an insect cell include Sf9 and Sf21, which are ovary cells of *Spodoptera frugiperda* ["Baculovirus Expression Vectors, A Laboratory Manual," W. H. Freeman and Company, New York (1992)], and High 5 (Invitrogen), which is an ovary cell of *Trichoplusia ni*.

The above-mentioned recombinant gene-introducing vector and the above-mentioned baculovirus can be co-transfected into an insect cell for the preparation of a recombinant virus by, for example, calcium phosphate method (JP-A Hei 2-227075), lipofection method [*Proc. Natl. Acad. Sci. USA,* 84, 7413 (1987)], and such.

When a plant cell is used as a host cell, examples of an expression vector are Ti plasmid and tobacco mosaic virus vector.

Any promoter may be used as long as it is able to function in a plant cell, and its examples are 35S promoter of cauliflower mosaic virus (CaMV) and rice actin 1 promoter.

Examples of the host cell are plant cells of tobacco, potato, tomato, carrot, soybean, rape, alfalfa, rice, wheat, and barley.

A recombinant vector can be introduced by any method as long as the method enables introduction of DNA into a plant cell, and its examples are a method using *Agrobacterium* (JP-A Sho 59-140885 and Sho 60-70080 and WO94/00977), electroporation method (JP-A Sho 60-251887), and a method using a particle gun (Japanese Patent Nos. 2606856 and 2517813).

Besides a direct expression, gene expression can be carried out by secretory production, fusion protein expression, and so on based on a method as described in Molecular Cloning Second Edition.

When the protein is expressed in yeast, animal cells, insect cells, or plant cells, it is possible to obtain the protein to which sugar or sugar chain is added.

The transformant prepared as above is cultured in a medium, and the protein of the present invention is produced and accumulated therein and collected from the culture, to produce the protein of the present invention. A method for culturing the transformant of the present invention in a medium can be carried out according to a common method used for culturing of the host.

A medium for culturing a transformant obtained using the bacteria such as *Escherichia coil* or eukaryotes such as yeast as a host, may be any of natural and synthetic media as long as the medium contains carbon source, nitrogen source, inorganic salts, and such, which can be assimilated by the organism and it enables culturing the transformant efficiently.

Any source may be used as a carbon source as long as the organism is able to assimilate it, and its examples are carbohydrates such as glucose, fructose, sucrose, molasses containing them, starch and hydrolyzed starch; organic acids such as acetic acid and propionic acid; and alcohols such as ethanol and propanol.

Examples of a nitrogen source include ammonia, ammonium salts of inorganic or organic acid such as ammonium chloride, ammonium sulfate, ammonium acetate, and ammonium phosphate, other nitrogen-containing compounds, peptone, meat extract, yeast extract, corn steep liquor, hydrolyzed casein, soybean cake, hydrolyzed soybean cake, various fermented cells and digested products thereof, and such.

Examples of an inorganic substance include potassium dihydrogen phosphate, dipotassium hydrogen phosphate, magnesium phosphate, magnesium sulfate, sodium chloride, ferrous sulfate, manganese sulfate, copper sulfate, calcium carbonate, and such.

Usually, the transformant is cultured under an aerobic condition, for example, by shake culture or submerged-aerated spinner culture. Temperature for the culturing is preferably 15 to 40° C., and time for the culturing is usually from 16 hours to seven days. The pH during the culturing is kept at 3.0 to 9.0. The pH is adjusted with inorganic or organic acid, an alkaline solution, urea, calcium carbonate, ammonia, etc.

During the culturing, an antibiotic such as ampicillin or tetracycline may be added to the medium if necessary.

In the case of culturing a microorganism transformed with a recombinant vector in which an inducible promoter is used as a promoter, an inducer may be added to the medium if necessary. For example, when a microorganism transformed with a recombinant vector in which lac promoter is used is cultured, isopropyl-β-D-thiogalactopyranoside and such may be added to the medium while, when a microorganism transformed with a recombinant vector containing trp promoter is cultured, indole acrylic acid and such may be added to the medium.

A medium for a transformant obtained using an animal cell as a host, can be the commonly used RPMI 1640 medium [*The Journal of the American Medical Association*, 199, 519 (1967)], Eagle's MEM medium [*Science*, 122, 501 (1952)], modified Dulbecco's MEM medium [*Virology*, 8, 396 (1959)], 199 medium [*Proceeding of the Society for the Biological Medicine*, 73, 1 (1950)], a medium prepared by adding fetal calf serum and such to any of these media, and the like.

The culturing is usually carried out for 1 to 7 days under the conditions, for example, of pH 6 to 8 at 30 to 40° C. in the presence of 5% $CO_2$.

During the culturing, an antibiotic such as kanamycin or penicillin may be added to the medium if necessary.

A medium for a transformant obtained using an insect cell as a host, can be the commonly-used TNM-FH medium (Pharmingen); Sf-900 II SFM medium (Life Technologies); ExCell400 and ExCell405 (both JRH Biosciences); Grace's Insect Medium (Grace, T. C. C., *Nature*, 195, 788 (1962)); and so on.

The culturing is usually carried out for 1 to 5 days under the conditions, for example, of pH 6 to 7 at 25 to 30°C.

During the culturing, an antibiotic such as gentamycin may be added to the medium if necessary.

A transformant obtained using a plant cell as a host can be cultured in the form of a cell or a differentiated cell or organ of the plant. A medium for the transformant, may be commonly used Murashige and Skoog (MS) medium, White medium, or a medium prepared by adding phytohormone such as auxin or cytokinin to any of these medium, and so on.

The culturing is usually carried out for 3 to 60 days under the conditions of pH 5 to 9 at 20 to 40°C.

During the culturing, an antibiotic such as kanamycin or hygromycin may be added to a medium if necessary.

As mentioned above, a trans formant derived from a microorganism, animal cell, or plant cell having a recombinant vector into which the DNA coding for the protein of the present invention is incorporated is cultured by a common culturing method, and the protein is produced and accumulated therein and is collected therefrom to obtain the protein.

Besides a direct expression, gene expression can be carried out by secretory production, fusion protein expression, and the like based on the method described in Molecular Cloning Second Edition, etc.

The method for producing the protein of the present invention includes intracellular production by host cells, extracellular secretion by host cells, or production on outer membranes by host cells, and the method can be selected depending on the host cells used or an alteration of the structure of the protein to be produced.

When the protein of the present invention is produced inside of the host cell or on an outer membrane of the host cell, it is possible to secrete the protein extracellular portion of the host cell according to the method of Paulson et al. [*J. Biol. Chem.*, 264, 17619 (1989)], the method of Row et al. [*Proc. Natl. Acad. Sci., USA*, 86, 8227 (1989); *Genes Develop.*, 4, 1288 (1990)], the methods described in JP-A Hei 5-336963 and 6-823021, etc.

Specifically, it is possible to secrete the protein of the present invention extracellular portion of the host cell by expressing the protein to which a signal peptide has been added to the upstream of the protein containing the active site of the protein by means of genetic engineering technique.

It is also possible to increase the production amount of the protein utilizing a gene-amplification system using a dihydrofolate reductase gene or the like according to the method described in JP-A Hei 2-227075.

(4) Preparation of Bacteria having a Lysozyme Sensitivity

A method for preparing bacteria having a lysozyme sensitivity by inactivating the activity of the protein of the present invention will be explained below.

Herein, the phrase "inactivating the activity of the protein of the present invention" means lowering or eliminating the activity of the protein of the present invention by, for example, disrupting a gene coding for the protein of the present invention; introducing a transposon into the gene; introducing an antisense gene into the gene; etc.

The gene which codes for the protein of the present invention is a nucleotide sequence having an information necessary for expression of activity of the protein of the present invention, and containing the promoter region, the open reading frame region, and the terminator region of the gene.

Examples of the bacteria used in this method are microorganisms belonging to the genus *Corynebacterium*, the genus *Brevibacterium*, the genus *Microbacterium*, the genus *Escherichia*, the genus *Serratia*, the genus *Bacillus*, the genus *Pseudomonas*; preferred examples are microorganisms belonging to the genus *Corynebacterium*, the genus *Brevibacterium*, or the genus *Microbacterium*; and more preferred examples are microorganisms belonging to the genus *Corynebacterium*.

A method for the preparation of bacteria having a lysozyme sensitivity using a microorganism belonging to the genus *Corynebacterium* will be mentioned below as an example.

It is possible to prepare a lysozyme-sensitive strain by introducing mutation such as substitution, deletion, and addition into a chromosomal gene coding for the protein of the present invention of the microorganism belonging to the genus *Corynebacterium* so that the activity of the protein of the present invention can be inactivated.

Mutation such as substitution, deletion, and addition to the chromosomal gene can be introduced by the following methods 1) and 2).

1) A recombinant plasmid is prepared by inserting the whole or a part of the DNA of the present invention into a plasmid which is unable to autonomously replicate in microorganisms belonging to the genus *Corynebacterium*. The prepared recombinant plasmid is introduced into the microorganism and, utilizing the homology in the sequence between the DNA and the chromosomal gene coding for the protein of the present invention, the recombinant plasmid is inserted into a homologous region on the chromosome. Alternatively, a part or the whole of the DNA inserted into the recombinant plasmid is substituted with the homologous region on the chromosome.

Examples of the plasmid which is unable to autonomously replicate in the microorganism are pSUP1021 [*J. Bacteriol.*, 178, 5768 (1996)] and pHSG298 (manufactured by Takara Shuzo).

2) A recombinant plasmid is prepared by inserting, under certain conditions, a part or the whole of the DNA of the present invention into a plasmid which is unable to autonomously replicate in the microorganism. The prepared recombinant plasmid is introduced into the microorganism and, under the conditions where the recombinant plasmid is unable to autonomously replicate, utilizing the homology in the sequence between the DNA and the chromosomal gene coding for the protein of the present invention, the recombinant plasmid is inserted into a homologous region on the chromosome. Alternatively, the whole or a part of the DNA inserted into the recombinant plasmid is substituted with a homologous region on the chromosome.

Examples of the plasmid which is unable to autonomously replicates in the microorganism under certain conditions are plasmids pHSC4, pHSC22, and pHSC23 (all described in JP-A Hei 7-203977), where the autonomous replication is sensitive to temperature.

In any of the above-mentioned methods, prior to the preparation of the recombinant plasmid, mutation such as substitution, deletion, and addition of a base can be introduced, by means of a site-directed mutagenesis, into a part or the whole of the DNA of the present invention to be inserted into the plasmid. When a drug-resistant gene such as kanamycin-resistant gene or a selective marker gene is inserted into the plasmid, it is easy to select a strain in which a homologous region is substituted.

As method for the introduction of a recombinant plasmid may be any method where DNA is introduced into the above host cell. Examples of such a method are protoplast method [JP-A Sho 57-186492 and Sho 58-56678; *J. Bacteriol.*, 159, 306 (1984)] and electroporation method (JP-A Hei 2-207791). It is also possible to introduce the plasmid from *Escherichia coli* into a microorganism belonging to the genus *Corynebacterium* by means of a conjugal transfer [*J. Bacteriol.*, 172, 1663 (1990); *J. Bacteriol.*, 178, 5768 (1996)].

When a selective marker gene such as a drug-resistant gene is inserted into a recombinant plasmid, it is possible that, after introduction of the plasmid into a host cell, the homologous recombinant strain is easily selected using a drug resistance and such as an index.

When kanamycin is used as a selective marker, the medium used for the selection of the homologous recombinant strain is a medium containing 1 to 800 µg/ml or, preferably, 3 to 100 µg/ml kanamycin such as LB medium [10 g/l Bactotrypton (manufactured by Difco), 5 g/l yeast extract (manufactured by Difco), and 5 g/l sodium chloride; pH 7.2] containing kanamycin of the above concentration.

By selecting a strain which grows in a kanamycin-containing medium, a homologous recombinant strain can be easily selected.

The strain selected by the above method is cultured at 20 to 39° C. for 24 to 72 hours in each of a common medium such as LB medium [10 g/l Bactotrypton (manufactured by Difco), 5 g/l yeast extract (manufactured by Difco), and 5 g/l sodium chloride; pH 7.2], and the medium further containing lysozyme.

A lysozyme-containing medium contains lysozyme in such a concentration that the lysozyme-sensitive microorganism shows sensitivity, for example, 0.5 to 50 µg/ml or, preferably, 1 to 25 µg/ml lysozyme.

According to the above method, a lysozyme-sensitive microorganism can be obtained as a strain which grows in a common medium but does not grow in a lysozyme-containing medium.

(5) Production of Amino Acid Using a Bacterium having a Lysozyme-Sensitivity

A method for the production of amino acid using a bacterium having a lysozyme-sensitivity will be explained below.

The bacterium having a lysozyme-sensitivity may be used for the production of any amino acid including acidic amino acids, neutral amino acids, and basic amino acids, but it is preferably used for the production of glutamic acid or glutamine.

In the present method, a common method for the production of amino acid by means of fermentation using bacteria such as microorganisms belonging to the genus *Corynebacterium*, the genus *Brevibacterium*, or the genus *Microbacterium* may be used except the use of the lysozyme-sensitive bacterium.

Specifically, an amino acid can be obtained by culturing the bacterium in a synthetic or natural medium containing carbon source, nitrogen source, inorganic substance, amino acid, vitamin, and so on under an aerobic condition at suitable temperature, pH, and such to produce and accumulate an amino acid in the culture, and collecting the amino acid.

Examples of the carbon source are carbohydrates such as glucose, fructose, sucrose, maltose, mannose, glycerol, starch, hydrolyzed starch solution, and molasses; polyalcohols; and organic acids such as pyruvic acid, fumaric acid, lactic acid, and acetic acid. Depending upon the assimilating property of the microorganism, hydrocarbon or alcohols may be used as well.

Examples of the nitrogen source are ammonia; inorganic and organic ammonium salts such as ammonium chloride, ammonium sulfate, ammonium carbonate, and ammonium acetate; and nitrogen-containing organic substances such as urea, peptone, NZ-amine, meat extract, yeast extract, corn steep liquor, hydrolyzed casein, fish meal, or a digested product thereof.

Examples of the inorganic substance are potassium dihydrogen phosphate, dipotassium hydrogen phosphate, ammonium sulfate, ammonium chloride, magnesium sulfate, sodium chloride, ferrous sulfate, manganese sulfate, and calcium carbonate.

Vitamins and amino acids used may differ depending upon the carbon source, nitrogen source, and such in the medium used and, if necessary, biotin, thiamine, glutamic acid, and so on may be used.

The culturing is carried out usually under an aerobic condition, for example, by shaking culture or aerated spinner culture, at 20 to 40° C. for 1 to 5 days.

After completion of the culturing, the cells are removed from the culture, and the resulting culture supernatant is treated by a known method such as treatment with active carbon or with ion-exchange resin, to collect an amino acid.

BEST MODE FOR CARRYING OUT THE INVENTION

Figure 1:
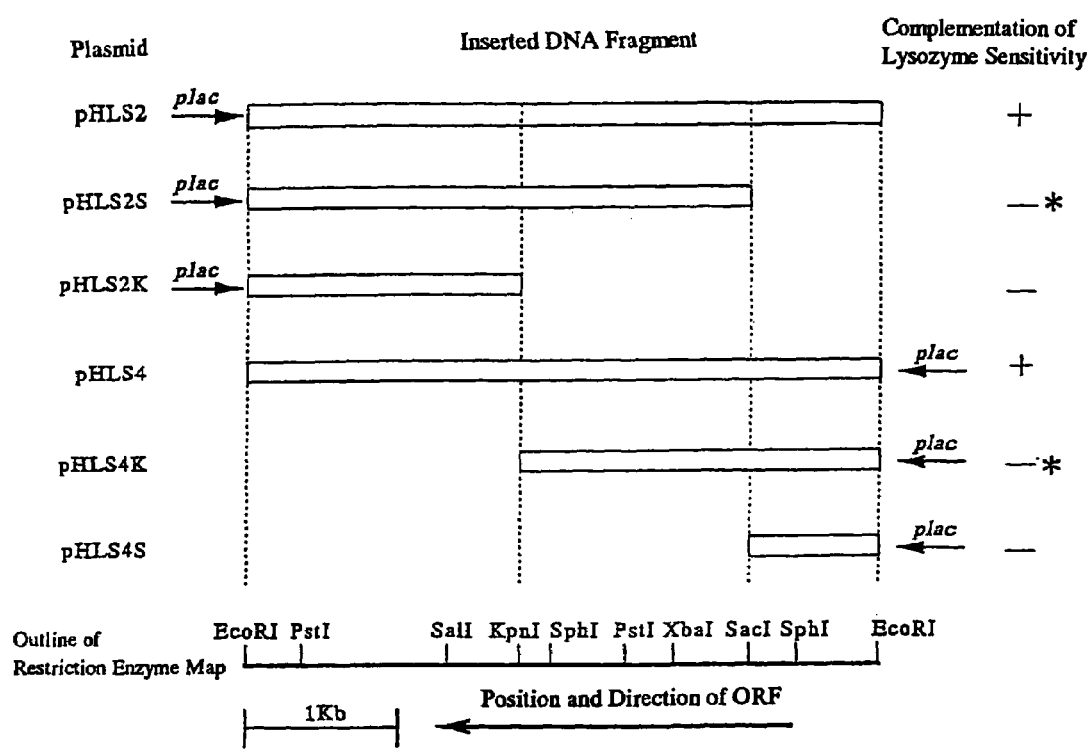
FIG. 1 shows the results of complementation tests for lysozyme sensitivity of *Corynebacterium glutamicum* KY9714 strain by using various deletion plasmids for the inserted DNA fragment of about 4 kb. "plac" shows a position of a lactose promoter existing on a vector pC2. "+" shows that lysozyme sensitivity is complemented while "–" shows that it is not. "*" shows that a complementation of a low frequency occurs due to homologous recombination with chromosome. An outline of the restriction enzyme map of the inserted DNA fragment of about 4 kb and the position and direction of an open reading frame (ORF) are shown in the figure.

Examples of the present invention will now be given below.

EXAMPLE 1

Preparation of Chromosomal DNA of *Corynebacterium Glutamicum* KY9611 Strain

*Corynebacterium glutamicum* KY9611 strain was inoculated on 10 ml of L' medium (1% polypeptone, 0.5% yeast extract, 0.5% sodium chloride, 0.1% glucose, and 20 μg/ml thiamine; pH 7.2) and cultured overnight at 30° C.

After the culturing, cells were collected from the resulting culture by centrifugation.

The cells were washed with TE buffer [50 mM Tris-HCl and 50 mM ethylenediaminetetraacetic acid (EDTA); pH 8.0] and suspended in 800 μl of the same buffer. To the suspension, 40 μl of 50 mg/ml lysozyme solution and 20 μl of 10 mg/ml RNase A solution were added, and the reaction was carried out at 37° C. for 1 hour. To the reaction solution, 20 μl of 20% sodium dodecylsulfate (SDS) solution was added, and the reaction was carried out at 70° C. for 1 hour. Proteinase K solution (20 mg/ml, 24 μl) was added, and the reaction was carried out at 50° C. for 1 hour. Further, 24 μl of the proteinase K solution was added thereto, and the reaction was carried out at 50° C. for 1 hour. To the resulting reaction solution, the same amount of phenol was added, and the mixture was stirred and allowed to stand overnight at 4° C. DNA was extracted into the aqueous layer, and the aqueous layer was recovered. To the aqueous layer, the same amount of phenol/chloroform was added, and the mixture was stirred. Extraction was carried out over 2 hours, and the aqueous layer was recovered. To the aqueous layer, the same amount of chloroform/isoamyl alcohol was added, and the mixture was stirred. Extraction was carried out over 30 minutes, and the aqueous layer was recovered. To the aqueous layer, a 2-fold amount of ethanol was added, and DNA was precipitated. The resulting precipitate was dissolved in 300 μl of TE buffer (10 mM Tris-HCl and 1 mM EDTA; pH 8.0) and was used as a chromosomal DNA.

EXAMPLE 2

Preparation of Gene Recovering Lysozyme Sensitivity

The chromosomal DNA (0.5 μg) obtained in Example 1 and 0.5 μg of plasmid pC2 were cleaved with EcoRI and subjected to a ligation reaction using a ligation kit (TaKaRa DNA Ligation Kit Ver.2 manufactured by Takara Shuzo) at 16° C. for 16 hours.

*Corynebacterium glutamicum* KY9714 strain was transformed using the ligation reaction solution according to the method described in Molecular Cloning Second Edition, and a transformant was selected utilizing temperature-sensitive growth of KY9714 strain. Specifically, the transformant was spread onto L' agar plate medium (prepared by adding 1.5% of agar to L' medium) containing 5 μl/ml kanamycin and cultivated at 37° C. for three days.

All of the resulting colonies showed a good growth on L' agar plate medium containing 100 μg/ml lysozyme, indicating that they were insensitive to lysozyme. The resulting colonies were cultured by the method described in Example 1, and the plasmid was recovered by the method described in Molecular Cloning Second Edition. The analysis of the structures of the recovered plasmids pHLS2 and pHLS4 revealed that each plasmid contained the same DNA fragment of about 4 kb derived from *Corynebacterium glutamicum* which was inserted into an EcoRI site of the plasmid pC2. The directions of the insertions in pHLS2 and pHLS4 are reverse to each other.

The sequence of the inserted DNA fragment of about 4 kb was determined. The determined nucleotide sequence of the EcoRI fragment of 3825 bp is shown in SEQ ID NO: 5. The nucleotide sequence determined as such contains an open reading frame (ORF) of 1920 bp comprising the nucleotide sequence as shown in SEQ ID NO:1 coding for the amino acid sequence of 640 amino acid residues as shown in SEQ ID NO:2. The nucleotide sequence as shown in SEQ ID NO:1 corresponds to the nucleotide sequence of from 815th to 2734th bases in the nucleotide sequence as shown in SEQ ID NO:3.

*Corynebacterium glutamicum* KY9714/pHLS4, carrying a plasmid pHLS4 containing DNA having the nucleotide sequence as shown by SEQ ID NO: 3, has been deposited as FERM BP-6479 since Sep. 1, 1998 at the National Institute of Bioscience and Human Technology, Agency of Industrial Science and Technology, 1-3Higashi-1-chome, Tsukuba-shi, Igaraki-ken, 305-8566 Japan.

Various deletion plasmids were prepared by a common method using the DNA fragment of about 4 kb inserted into the resulting plasmid, and a complementation test for lysozyme sensitivity of *Corynebacterium glutamicum* KY9714 strain was carried out. It was found that the ORF of 1920 bp comprising 640 amino acid residues found was essential for a complementation of lysozyme sensitivity (FIG. 1).

A complementation test using pHLS2S lacking EcoRI-SacI fragment of about 1 kb in the DNA insert of about 4 kb, and pHLS4K lacking EcoRI-KpnI fragment of about 1.4 kb in the DNA insert of about 4 kb, showed a complementation of lysozyme sensitivity at a low frequency presumed to be due to a homologous recombination with chromosomal DNA (FIG. 1).

This means that, in the ORF of 1920 bp, there is a mutation causative of lysozyme sensitivity of *Corynebacterium glutamicum* KY9714 strain introduced in a SacI-KpnI fragment of about 1.2 kb, which corresponds to the nucleotide of from 271st to 1593rd in the nucleotide sequence shown by SEQ ID NO:1.

EXAMPLE 3

Identification of Mutation Point of Lysozyme-Sensitive Strain

A chromosomal DNA of *Corynebacterium glutamicum* KY9714 strain was prepared by the same method as in Example 1. Based upon a finding that the SacI-KpnI fragment of about 1.2 kb of Example 2 includes a mutation causative of lysozyme sensitivity of *Corynebacterium glutamicum* KY9714 strain, PCR was carried out using a chromosomal DNA of KY9714 strain as a template and using the DNA described in SEQ ID NO: 6, corresponding to the 70th to 77th amino acid residues from the N-terminus of the ORF of 1920 bp, and the DNA described in SEQ ID NO: 5, corresponding to the 335th to 342nd amino acid residues from the N-terminus of the same, as primers.

The PCR was carried out using TaKaRa LA PCR Kit Ver. 2.2 for 29 cycles where one cycle contains the reaction steps of 94° C. for one minute, 98° C. for 20 seconds, 50° C. for 30 seconds, and 62° C. for 3 minutes, and then the reaction was further carried out at 70° C. for 10 minutes.

The reaction solution was subjected to agarose gel electrophoresis, and the DNA fragments of about 0.8 kb produced as a result of the PCR were extracted by the method described in Molecular Cloning Second Edition to recover the DNA fragments. The DNA fragments were cleaved with SalI and SphI, then mixed with the plasmid pHSG398 (manufactured by Takara Shuzo) cleaved with SalI and SphI and subjected to a ligation reaction at 16° C. for 16 hours using a ligation kit (TaKaRa DNA Ligation Kit ver.2; manufactured by Takara Shuzo). *Escherichia coli* JM109 strain (manufactured by Stratagene) was transformed according to the method described in Molecular Cloning Second Edition using the above reaction solution.

A plasmid was extracted from the resulting transformant, and the nucleotide sequence of the SalI-SphI DNA fragment of about 0.8 kb inserted into the plasmid was determined. Comparing this sequence with the corresponding region of the DNA obtained from KY9611 strain in Example 2, it was found that a codon coding for tryptophan, which was the 132nd amino acid in the ORF (SEQ ID NO: 1) of 1920 bp coding for the protein (SEQ ID NO: 2) of 640 amino acids, was changed from TGG to TAG in the KY9714 strain.

EXAMPLE 4

Complementation of Lysozyme-Sensitivity

The plasmid pHLS2, obtained in Example 2, was introduced into each of various lysozyme-sensitive strains such as lysozyme-sensitive strains ATCC 31834 strain, KY 11939 strain, KY 11940 strain, and KY 11941 strain derived from *Corynebacterium glutamicum* KY9611 strain and also lysozyme-sensitive strains KY 9704 strain and KY 9706 strain derived from *Corynebacterium glutamicum* ATCC 13032 strain, and the changes in the lysozyme sensitivity were tested.

No growth was observed for all of the above-mentioned lysozyme-sensitive strains in L' agar plate medium containing 12.5 µg/ml lysozyme. On the other hand, the transformants prepared by introduction of pHLS2 into such strains showed good growth even in L' agar plate medium containing 100 µg/ml lysozyme.

The above results show that, in all of mutants, the lysozyme sensitivity was complemented by the ORF of 1920 bp having 640 amino acid residues and that the mutation of the ORF is a cause of lysozyme sensitivity.

EXAMPLE 5

Production of Glutamic Acid and Glutamine Using Lysozyme-Sensitive Strains

Glutamic acid and glutamine were produced in a medium containing an excessive amount of biotin using lysozyme-sensitive KY 9704 strain and KY 9706 strain, derived from *Corynebacterium glutamicum* ATCC 13032 strain.

Each of KY 9704 strain and KY 9706 strain was cultivated in 10 ml of L' medium at 30° C. for 24 hours, and 0.5 ml of the resulting seed culture was inoculated in 10 ml of a medium (pH 7.0) composed of 50 g/l glucose, 3 g/l $(NH)_2SO_4$, 3 g/l urea, 0.5 g/l $KH_2PO_4$, 0.5 g/l $K_2HPO_4$, 0.5 g/l $MgSO_4 \cdot 7H_2O$, 10 mg/l $FeSO_4 \cdot 7H_2O$, 10 mg/l $MnSO_4 \cdot 4H_2O$, 100 µg/l biotin, 500 µg/l thiamine hydrochloride, and 10 mg/l Phenol Red, and cultured at 30° C. for 48 hours.

After the culturing, the amounts of glutamic acid and glutamine produced in the medium were measured. In KY 9704 strain, 4.5 g/l glutamic acid was accumulated, while, in KY 9706 strain, 9.0 g/l glutamine was accumulated.

The transformants which were prepared by introduction of pHLS2 into each of ATCC 13032 strain (parent strain), KY 9704 strain, and KY 9706 strain under the same conditions were cultured under the same condition as above and the amounts of produced glutamic acid and glutamine were measured. In any of the transformants, accumulation of glutamic acid and glutamine was not observed.

The above results show that it is possible to produce glutamic acid and glutamine in a medium containing an excessive biotin by introducing (a) mutation(s) in an ORF of 1920 bp coding for the above 640 amino acid residue.

EXAMPLE 6

Preparation of Qene-Disrupted Strain of *Corynebacterium Glutamicum*

The DNA fragment obtained in Example 2 was cleaved with SalI and PstI and, by the method described in Molecular cloning Second Edition, the SalI-PstI fragment of about 1.2 kb was obtained. The recovered DNA and the plasmid pHSG298 (manufactured by Takara Shuzo) cleaved with SalI and PstI (manufactured by Takara Shuzo) were mixed and subjected to a ligation reaction at 16° C. for 16 hours using a ligation kit (TaKaRa DNA Ligation Kit ver. 2; manufactured by Takara Shuzo). *Corynebacterium glutamicum* KY 9611 strain was transformed using the reaction solution according to the method described in Molecular Cloning Second Edition.

The transformant was spread onto L' agar plate medium containing 10 μl/ml of kanamycin and cultivated at 30° C. for 2 days.

From the colonies generated after the cultivation, a chromosomal DNA was obtained according to the method described in Example 1. PCR was carried out using the resulting chromosomal DNA as a template according to the method described in Example 3 and using M13 Primer RV (manufactured by Takara Shuzo), having the nucleotide sequence shown by SEQ ID NO: 6 corresponding to the plasmid pHSG298, and the DNA described in SEQ ID NO: 4, corresponding to 70th to 77th amino acid residues from the N-terminus of the protein having the amino acid sequence shown by SEQ ID NO: 2, as primers. In all of the transformants, fragments of about 1.65 kb were obtained.

Figure 2:
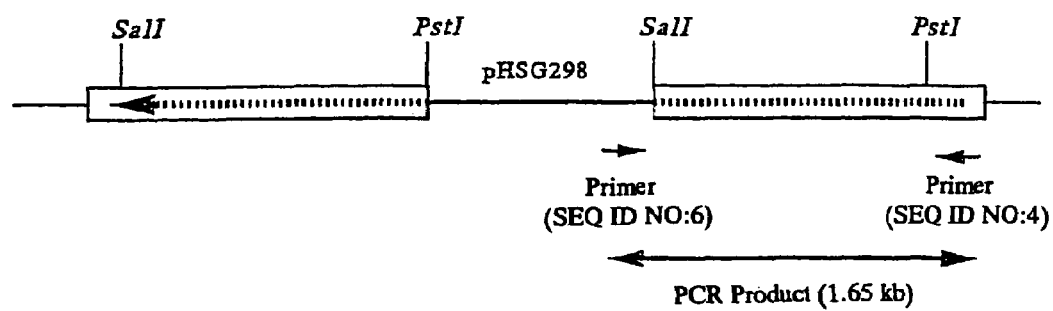
FIG. 2 shows an outline of the chromosomal structure of a gene-disrupted strain. The bold line shows the vector (pHSG298), and the arrow with the dotted line shows the position and direction of the ORF. The type and position of the primer and the size and position of the PCR product are shown in the figure.

The above results show that, due to the homology with the SalI-PstI region of about 1.2 kb, pHSG298 was incorporated into the ORF of 1920 bp on the chromosome and the ORF was disrupted (FIG. 2).

Growth of all of the gene-disrupted strains obtained as such was not observed on L' agar plate medium containing 12.5 μg/ml lysozyme.

The above results show that lysozyme-sensitive microorganism can be efficiently obtained by disrupting the ORF of 1920 bp on chromosome.

INDUSTRIAL APPLICABILITY

The present invention provides a protein having an activity of giving a lysozyme insensitivity to a lysozyme-sensitive microorganism belonging to *Corynebacterium glutamicum*; DNA which codes for the protein; a recombinant vector containing the DNA; a transformant obtained by introducing the recombinant vector into a host cell; a bacterium having a lysozyme sensitivity in which the activity of the protein is inactivated; and a method for the production of an amino acid using the bacterium.

The invention claimed is:

1. A method of producing glutamic acid or glutamine, said method comprising:
   (i) inducing lysozyme sensitivity of a microorganism, which belongs to a genus *Corynebacterium*, which has an ability to produce glutamic acid or glutamine, and which is insensitive to lysozyme, by
      (a) inactivating a protein comprising SEQ ID NO: 2, or
      (b) inactivating a protein encoded by a DNA hybridizing with a DNA, that has a complementary nucleotide sequence of SEQ ID NO: 1, at 65° C. in the presence of 0.7 to 1.0 M sodium chloride and encoding a protein which cause lysozyme insensitivity in said microorganism, wherein the hybridization further includes a step of washing under the condition of 65° C. by the use of solution containing 15 to 300 mM sodium chloride and 1.5 to 30 mM sodium citrate and thus causing lysozyme sensitivity in said microorganism to produce a lysozyme-sensitive microorganism, wherein said inducing is not caused by a random mutation but caused by gene disruption, introduction of a transposon, introduction of an antisense gene, homologous recombination or homologous insertion;
   (ii) culturing said lysozyme-sensitive microorganism of (i);
   (iii) producing and accumulating glutamic acid or glutamine in said culture; and
   (iv) collecting said glutamic acid or glutamine from said culture.

2. A method of producing glutamic acid or glutamine according to claim 1, wherein the microorganism belonging to the genus *Corynebacterium* is *Corynebacterium glutamicum*.

3. A method of producing glutamic acid or glutamine, said method comprising:
   (i) inducing lysozyme sensitivity of a microorganism which belongs to a genus *Corynebacterium*, which has an ability to produce glutamic acid or glutamine, and which is insensitive to lysozyme, by introducing a mutation into a chromosome gene, wherein said inducing is not caused by a random mutation but caused by gene disruption, introduction of a transposon, introduction of an antisense gene, homologous recombination or homologous insertion to inactivate a protein encoded by said chromosome gene to produce a lysozyme-sensitive microorganism, wherein said chromosome gene is
      (a) a chromosome gene encoding a protein comprising SEQ ID NO: 2,
      (b) a chromosome gene comprising SEQ ID NO: 1, or
         (c) a chromosome gene hybridizing with a DNA having a complementary nucleotide sequence of SEQ ID NO: 1 at 65° C. in the presence of 0.7 to 1.0 M sodium chloride and encoding a protein which causes lysozyme insensitivity in said microorganism, wherein the hybridization further includes a step of washing under the condition of 65° C. by the use of solution containing 15 to 300mM sodium chloride and 1.5 to 30mM sodium citrate;
   (ii) culturing said lysozyme-sensitive microorganism of (i) which is induced lysozyme sensitivity;
   (iii) producing and accumulating glutamic acid or glutamine in said culture; and
   (iv) collecting said glutamic acid or glutamine from said culture.

4. A method of producing glutamic acid or glutamine according to claim 3, wherein the microorganism belonging to the genus *Corynebacterium* is *Corynebacterium glutamicum*.

* * * * *

SEQUENCE LISTING

```
<160> NUMBER OF SEQ ID NOS: 6

<210> SEQ ID NO 1
<211> LENGTH: 1920
<212> TYPE: DNA
<213> ORGANISM: Corynebacterium glutamicum

<400> SEQUENCE: 1
atgtgcggcc ttcttggcat attgactgca aatgggaacg ctgaagcatt cgttcctgca      60
ctcgagcggg ccttgccatg catgcgccac cgtggtcctg acgatgccgg cacttggcat     120
gacgccgatg cagcgtttgg attcaaccgc ctctccatca ttgatattgc acactcccac     180
caaccactgc gttggggacc tgcggatgaa cccgaccgct acgcaatgac tttcaacggt     240
gagatctaca actacgttga gctgcgtaaa gagctctcgg atttgggata tacctttaat     300
acttctggcg atggcgagcc aattgttgtc ggtttccacc actggggcga gtccgtggtc     360
gagcatctcc gcggaatgtt cggcattgcc atttgggata caaaggaaaa gtcgcttttc     420
cttgcgcgtg atcagttcgg catcaagcca ctgttctacg caaccaccga gcatggcacc     480
gtgttctcct cagagaagaa gaccatcttg gagatggccg aggagatgaa tctagatctg     540
ggccttgata agcgcaccat tgagcactac gtggacctgc agtacgtgcc cgagccagat     600
acccttcacg cgcagatttc ccgcttggag tcaggctgca ccgcaacagt tcgtccgggc     660
ggcaagctgg aacagaagcg ttacttcaag cctcagttcc cagtacagaa ggtcgtaaag     720
ggtaaggagc aggacctctt cgatcgcatt gcccaggtgt tggaggatag cgtcgaaaag     780
catatgcgtg ccgacgtgac cgtaggctcg ttcctttccg gcggcattga ctcaaccgca     840
attgcgccgc ttgcaaagcg ccacaaccct gacctgctca ccttcaccac cggtttcgag     900
cgtgaaggct actcggaggt cgatgtggct gcggagtccg ccgctgcgat tggcgctgag     960
cacatcgtga agattgtctc gcctgaggaa tacgccaacg cgattcctaa gatcatgtgg    1020
tacttggatg atcctgtagc tgacccatca ttggtcccgc tgtacttcgt ggcagcgaa     1080 gcacgtaagc acgtcaaggt tgtgctgtct ggcgagggcg cagatgagct gttcggtgga    1140
```

```
tacaccattt acaaagagcc gctatcgctt gctccatttg agaagatccc ttccccacta    1200
cgtaaaggcc tgggaaagct cagcaaggtt ctgccagacg gcatgaaggg caagtccctt    1260
cttgagcgtg gctccatgac catggaagag cgctactacg gcaacgctcg ctccttcaat    1320
ttcgagcaga tgcaacgcgt tattccatgg gcaaagcgcg aatgggacca ccgcgaagtc    1380
actgcaccga tctacgcaca atcccgcaac tttgatccag tagcccgcat gcaacacctg    1440
gatctgttca cctggatgcg cggcgacatc ctggtcaagg ctgacaagat caacatggcg    1500
aactcccttg agctgcgagt tccattcttg gataaggaag ttttcaaggt tgcagagacc    1560
attccttacg atctgaagat tgccaacggt accaccaagt acgcgctgcg cagggcactc    1620
gagcagattg ttccgcctca cgttttgcac cgcaagaagc tgggcttccc tgttcccatg    1680
cgccactggc ttgccggcga tgagctgttc ggttgggcgc aggacaccat taaggaatcc    1740
ggtactgaag atatcttcaa caagcaggct gtgctggata tgctgaacga gcaccgcgat    1800
ggcgtgtcag atcattcccg tcgactgtgg actgttctgt catttatggt gtggcacggc    1860 attttgtgg aaaaccgcat tgatccacag attgaggacc gctcctaccc ggtcgagctt    1920
```

<210> SEQ ID NO 2
<211> LENGTH: 640
<212> TYPE: PRT
<213> ORGANISM: Corynebacterium glutamicum

<400> SEQUENCE: 2

```
Met Cys Gly Leu Leu Gly Ile Leu Thr Ala Asn Gly Asn Ala Glu Ala
 1               5                  10                  15

Phe Val Pro Ala Leu Glu Arg Ala Leu Pro Cys Met Arg His Arg Gly
                20                  25                  30

Pro Asp Asp Ala Gly Thr Trp His Asp Ala Asp Ala Ala Phe Gly Phe
            35                  40                  45

Asn Arg Leu Ser Ile Ile Asp Ile Ala His Ser His Gln Pro Leu Arg
        50                  55                  60

Trp Gly Pro Ala Asp Glu Pro Asp Arg Tyr Ala Met Thr Phe Asn Gly
 65                  70                  75                  80

Glu Ile Tyr Asn Tyr Val Glu Leu Arg Lys Glu Leu Ser Asp Leu Gly
                85                  90                  95

Tyr Thr Phe Asn Thr Ser Gly Asp Gly Glu Pro Ile Val Val Gly Phe
               100                 105                 110

His His Trp Gly Glu Ser Val Val Glu His Leu Arg Gly Met Phe Gly
            115                 120                 125

Ile Ala Ile Trp Asp Thr Lys Glu Lys Ser Leu Phe Leu Ala Arg Asp
        130                 135                 140

Gln Phe Gly Ile Lys Pro Leu Phe Tyr Ala Thr Thr Glu His Gly Thr
145                 150                 155                 160

Val Phe Ser Ser Glu Lys Lys Thr Ile Leu Glu Met Ala Glu Glu Met
                165                 170                 175

Asn Leu Asp Leu Gly Leu Asp Lys Arg Thr Ile Glu His Tyr Val Asp
            180                 185                 190

Leu Gln Tyr Val Pro Glu Pro Asp Thr Leu His Ala Gln Ile Ser Arg
        195                 200                 205

Leu Glu Ser Gly Cys Thr Ala Thr Val Arg Pro Gly Gly Lys Leu Glu
    210                 215                 220

Gln Lys Arg Tyr Phe Lys Pro Gln Phe Pro Val Gln Lys Val Val Lys
225                 230                 235                 240
```

-continued

```
Gly Lys Glu Gln Asp Leu Phe Asp Arg Ile Ala Gln Val Leu Glu Asp
                245                 250                 255
Ser Val Glu Lys His Met Arg Ala Asp Val Thr Val Gly Ser Phe Leu
            260                 265                 270
Ser Gly Gly Ile Asp Ser Thr Ala Ile Ala Pro Leu Ala Lys Arg His
        275                 280                 285
Asn Pro Asp Leu Leu Thr Phe Thr Thr Gly Phe Glu Arg Glu Gly Tyr
    290                 295                 300
Ser Glu Val Asp Val Ala Ala Glu Ser Ala Ala Ala Ile Gly Ala Glu
305                 310                 315                 320
His Ile Val Lys Ile Val Ser Pro Glu Glu Tyr Ala Asn Ala Ile Pro
                325                 330                 335
Lys Ile Met Trp Tyr Leu Asp Asp Pro Val Ala Asp Pro Ser Leu Val
            340                 345                 350
Pro Leu Tyr Phe Val Ala Ala Glu Ala Arg Lys His Val Lys Val Val
        355                 360                 365
Leu Ser Gly Glu Gly Ala Asp Glu Leu Phe Gly Gly Tyr Thr Ile Tyr
    370                 375                 380
Lys Glu Pro Leu Ser Leu Ala Pro Phe Glu Lys Ile Pro Ser Pro Leu
385                 390                 395                 400
Arg Lys Gly Leu Gly Lys Leu Ser Lys Val Leu Pro Asp Gly Met Lys
                405                 410                 415
Gly Lys Ser Leu Leu Glu Arg Gly Ser Met Thr Met Glu Glu Arg Tyr
            420                 425                 430
Tyr Gly Asn Ala Arg Ser Phe Asn Phe Glu Gln Met Gln Arg Val Ile
        435                 440                 445
Pro Trp Ala Lys Arg Glu Trp Asp His Arg Glu Val Thr Ala Pro Ile
    450                 455                 460
Tyr Ala Gln Ser Arg Asn Phe Asp Pro Val Ala Arg Met Gln His Leu
465                 470                 475                 480
Asp Leu Phe Thr Trp Met Arg Gly Asp Ile Leu Val Lys Ala Asp Lys
                485                 490                 495
Ile Asn Met Ala Asn Ser Leu Glu Leu Arg Val Pro Phe Leu Asp Lys
            500                 505                 510
Glu Val Phe Lys Val Ala Glu Thr Ile Pro Tyr Asp Leu Lys Ile Ala
        515                 520                 525
Asn Gly Thr Thr Lys Tyr Ala Leu Arg Arg Ala Leu Glu Gln Ile Val
    530                 535                 540
Pro His Val Leu His Arg Lys Leu Gly Phe Pro Val Pro Met
545                 550                 555                 560
Arg His Trp Leu Ala Gly Asp Glu Leu Phe Gly Trp Ala Gln Asp Thr
                565                 570                 575
Ile Lys Glu Ser Gly Thr Glu Asp Ile Phe Asn Lys Gln Ala Val Leu
            580                 585                 590
Asp Met Leu Asn Glu His Arg Asp Gly Val Ser Asp His Ser Arg Arg
        595                 600                 605
Leu Trp Thr Val Leu Ser Phe Met Val Trp His Gly Ile Phe Val Glu
    610                 615                 620
Asn Arg Ile Asp Pro Gln Ile Glu Asp Arg Ser Tyr Pro Val Glu Leu
625                 630                 635                 640
```

<210> SEQ ID NO 3
<211> LENGTH: 3825

<210> TYPE: DNA
<213> ORGANISM: Corynebacterium glutamicum

<400> SEQUENCE: 3

```
gaattcaccc tcgccacgct tttcagccct ctttgcgccc caggcaaaga tggcggtgag      60
gaatagaccc cacatgatga tgccgatgat ccaggcagca acccagaccc atgaccagaa     120
gttacccatg ccactgctt cagggtaat gccatcaggc caacccatac gtaggaaatc       180
tccaagcaca ccgccagagg ggcgacttca cagcctgcga tggcgaggcc acctaagctc     240
aagacaccgc caagcaggc cttgcgcttt aaaccacgct tattttgctg ttctacgtgt      300
gttctgcctt cctgtccaca caaaaaccag agaccttacg gtcatttcta tcttcgcaga    360
atagcctatt tgccagccga ttccatatct tgtgtttggt ggaaatatct tcgtgggttt    420
cgttttagg ggcgtcaaat gtcttcaac tgcaacgata tgcccgaatc ctcaggtgga      480
atacctaaag tctaggcaat tggtgtatgc cacgtcacag accatcaacc ttttgattgc    540
ccttgaaatt cccccaccct tacccctac gttcctacaa ggtgcatgta ttaggaaatc     600
aatctggttt tcaggaacct ttgaggatgc tgcaatagtc agctgatgca cgttgtttga    660
gggagctttc gtcaattttg gcgtgccctt ttcacctcag atgtaacttc gccgtatcgt    720
tgacacgaga tttaacaaat gcagcgtctt atttcttcca acaaaatttc tttgcgattt     780
aaggcgcctt ttatttcagg aggatttttc attcatgtgc ggccttcttg gcatattgac    840
tgcaaatggg aacgctgaag cattcgttcc tgcactcgag cgggccttgc catgcatgcg    900
ccaccgtggt cctgacgatg ccggcacttg gcatgacgcc gatgcagcgt ttggattcaa    960
ccgcctctcc atcattgata ttgcacactc ccaccaacca ctgcgttggg gacctgcgga   1020
tgaacccgac cgctacgcaa tgactttcaa cggtgagatc tacaactacg ttgagctgcg   1080
taaagagctc tcggatttgg gatataccct taatacttct ggcgatggcg agccaattgt   1140
tgtcggtttc caccactggg gcgagtccgt ggtcgagcat ctccgcggaa tgttcggcat   1200
tgccatttgg gatacaaagg aaaagtcgct tttccttgcg cgtgatcagt tcggcatcaa   1260
gccactgttc tacgcaacca ccgagcatgg caccgtgttc tcctcagaga agaagaccat   1320
cttggagatg gccgaggaga tgaatctaga tctgggcctt gataagcgca ccattgagca   1380
ctacgtggac ctgcagtacg tgcccgagcc agatacccct tcacgcgcaga tttcccgcctt   1440
ggagtcaggc tgcaccgcaa cagttcgtcc gggcggcaag ctggaacaga agcgttactt   1500
caagcctcag ttcccagtac agaaggtcgt aaagggtaag gagcaggacc tcttcgatcg   1560
cattgcccag gtgttggagg atagcgtcga aaagcatatg cgtgccgacg tgaccgtagg   1620
ctcgttcctt tccggcggca ttgactcaac cgcaattgcg ccgcttgcaa agcgccacaa   1680
ccctgacctg ctcaccttca ccaccggttt cgagcgtgaa ggctactcgg aggtcgatgt   1740
ggctgcggag tccgccgctg cgattggcgc tgagcacatc gtgaagattg tctcgcctga   1800
ggaatacgcc aacgcgattc ctaagatcat gtggtacttg gatgatcctg tagctgaccc   1860
atcattggtc ccgctgtact tcgtggcagc ggaagcacgt aagcacgtca aggttgtgct   1920
gtctggcgag ggcgcagatg agctgttcgg tggatacacc atttacaaag agccgctatc   1980
gcttgctcca tttgagaaga tcccttcccc actacgtaaa ggcctgggaa agctcagcaa   2040
ggttctgcca gacggcatga agggcaagtc ccttcttgag cgtggctcca tgaccatgga   2100
agagcgctac tacggcaacg ctcgctcctt caatttcgag cagatgcaac gcgttattcc   2160
atgggcaaag cgcgaatggg accaccgcga agtcactgca ccgatctacg cacaatcccg   2220
```

```
caactttgat ccagtagccc gcatgcaaca cctggatctg ttcacctgga tgcgcggcga    2280
catcctggtc aaggctgaca agatcaacat ggcgaactcc cttgagctgc gagttccatt    2340
cttggataag gaagttttca aggttgcaga gaccattcct tacgatctga agattgccaa    2400
cggtaccacc aagtacgcgc tgcgcagggc actcgagcag attgttccgc ctcacgtttt    2460
gcaccgcaag aagctgggct tccctgttcc catgcgccac tggcttgccg gcgatgagct    2520
gttcggttgg gcgcaggaca ccattaagga atccggtact gaagatatct tcaacaagca    2580
ggctgtgctg gatatgctga cgagcaccg cgatggcgtg tcagatcatt cccgtcgact     2640
gtggactgtt ctgtcattta tggtgtggca cggcatttt gtggaaaacc gcattgatcc     2700
acagattgag gaccgctcct acccggtcga gctttaagtc ttaaagccta aaccccctcc    2760
ttctcaagga gggggtttca ctatttcctg aggacaaagc aattacgcca gcaaacacaa    2820
aagctcggcc gtagacaatg cgtccagggc cgagccttta ttcctatata acggaatctc    2880
tttagttgaa ggagtcacca caagcgcaag agctgcctgc gtttggttg tcgatggtga     2940 agccctgctg ctcgatggtg tcagcgaagt cgatctgagc gccgagcagg tatggggtgc    3000
tcatcttgtc aacgacaagg cgaacgccac cgacgatgtc ttccttatcg ccatcaaggg    3060
tgcggtcgtc gaagtaaagc tggtaacgaa ggccagagca gccgccaggc tgaacggcga    3120
tacgcagaga gaggtcgtcg cggccttcct gatcgatgag tgccttagct ttggacgctg    3180
cggactcggt caagataaca ccggtgttgg ttgatggagc ggtcatcgct ttagtctcct    3240
taactgttgg ccctttgaat tacttttagg ccgggacatc ataggcttgc agtgtactcc    3300
cctttttacg gatctccggc gagcgatgct ggattacgtt catatgggaa gcggatggat    3360
gttccccagc ctactcaccg tccacagatg agtaaacccg gaaaaacccg tatttagtta    3420
ttggttttac ctgcgtgggc tgaaagtctt cacttttaat ccttacagat ggtcgttctg    3480
attcctttca acgatgaagt gtgcacccct attcccgatt tgggaggttt tccttgtagc    3540
ctattgagtg tgaaacttcc ttgggataaa aataagaaca acgaagggc tgacgctgca     3600 ggccaagacg ccagctccac ccctgagacc gctacgcctg acgctactga gcagaaattg    3660 ccaaggggc acacggcacc gaagggccgt cccactccga agcgtcgtga agttgagtta     3720
gagcgaggtg tcgttggcgg ccagtctttg gcgcctactg atacttatgc gcagcagcgc    3780
cagaagcgta aagaatttaa agcatctatg accaaggaag aattc                    3825
```

```
<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
tgaacccgac cgcatgccaa tgact                                           25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
tccaaggtcg acatgatctt aggaa                                           25
```

```
<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
caggaaacag ctatgac                                                    17
```